United States Patent [19]

Sherman et al.

[11] Patent Number: 5,474,912

[45] Date of Patent: Dec. 12, 1995

[54] METHOD FOR INCREASING PRODUCTION OF MICROBIAL METABOLITES BY GENETIC ENGINEERING

[76] Inventors: David H. Sherman, 2248 Drew Ave. South, St. Louis Park, Minn. 55416; Wei-Shou Hu, 1810 Howell St., Falcon Heights, Minn. 55113; Li-Hong Malmberg, 2742 Arthur St., NE., Minneapolis, Minn. 55418

[21] Appl. No.: 206,006

[22] Filed: Mar. 3, 1994

[51] Int. Cl.$^6$ ............................ C12N 1/15; C12N 1/21; C12P 35/06; C12P 37/00

[52] U.S. Cl. ............................ 435/43; 435/47; 435/48; 435/49; 435/172.3; 435/252.3; 435/252.33; 435/252.34; 435/252.35; 435/254.1; 435/254.5

[58] Field of Search ........................ 435/170, 171, 435/172.3, 252.3, 254.1, 252.33, 252.34, 252.35, 254.5, 43, 47, 48, 49; 424/115

[56] References Cited

U.S. PATENT DOCUMENTS 5,108,918  4/1992  Groenen et al. ..................... 435/172.3

OTHER PUBLICATIONS

Malmberg et al. (1991), Biotechnol. Bioeng. 38(8): 941–947.
Malmberg et al. (1992), Appl. Microbiol. Biotechnol. 38: 122–128.
Scherer et al. (1979), Proc. Natl. Acad. Sci. USA 76(10): 4951–4955.
Paul L. Skatrud, et al., Bio–Technology, 7, May 1989, pp. 477–485.
Paul L. Skatrud, et al., Poster Presentation 1987 Annual Meeting of Society of Industrial Microbiology, Baltimore, Aug. 1987, Abstract publ. in SIM News, vol. 37, No. 4, Jul./Aug. 1987.
L. M. Luengo, et al., J. Bacteriol., 144: 869–76 (1980).
P. S. Masurekar et al., Can. J. Microbiol., 18, 1045–1048 (1972).
S. Mendelovitz et al., Antimicrob. Agents Chemother., 21: 74–84 (1982).
M. B. Tobin et al., Journal of Bacteriology, vol. 173, No. 19, Oct. 1991, pp. 6223–6229.
S. Mendelovitz et al., Journal of General Microbiology, 1983, 129, 2063–2069.
Am. Chemical Society, Division of Biochemical Technology, 205th ACS National Meeting, Mar. 28–Apr. 2, 1993, Paper No. 11.
L. Malmberg, et al., Journal of Bacteriology, Nov. 1993, pp. 6916–6924.

Primary Examiner—Mindy Fleisher
Assistant Examiner—Philip W. Carter
Attorney, Agent, or Firm—Lorraine R. Sherman

[57] ABSTRACT

Targeted gene insertion methodology can increase the production of an antimicrobial metabolite and comprises the steps of:

a) identifying the gene in unaltered chromosomal DNA which encodes an enzyme that catalyzes the rate controlling step in a biosynthetic pathway in the production of increased concentration of a precursor to a core molecule which leads to the antimicrobial metabolite; and b) inserting into unaltered chromasomal DNA a genetic delivery vehicle (such as a vector, phage, or virus) which carries a gene which encodes the enzyme that catalyzes the rate controlling step in the biosynthesis in the production of a core molecule which is a precursor to the antimicrobial metabolite into unaltered chromosomal DNA, said delivery vehicle being compatible with said unaltered chromosomal DNA, the delivery vehicle being generated by inserting at least one exact or modified copy of the gene determining the rate controlling step into the compatible delivery vehicle, and inserting the delivery vehicle containing the gene into the unaltered chromosomal DNA so that the resulting altered chromosomal DNA has increased genetic material for performing the rate controlling function.

18 Claims, 8 Drawing Sheets wild-type wild-type

5,474,912

METHOD FOR INCREASING PRODUCTION OF MICROBIAL METABOLITES BY GENETIC ENGINEERING

This invention was made in part using government support under National Science Foundation Grant No. BCS-8552670 and the government has certain rights in the invention.

TECHNICAL FIELD

This invention relates to a method for increasing production of microbial metabolites by genetic engineering. In another aspect, it relates to a chromosome comprising a targeted genetic insertion of DNA.

BACKGROUND ART

Over the past 50 years, pharmaceuticals have been developed directly from microbial sources and have had an important influence on health care throughout the world. For example, the penicillin antibiotics have had an enormous impact on the control of bacterial infections in humans and animals. In addition to antibacterial activity, other classes of microbial agents have been discovered and developed that have, for example, antifungal, anticancer, and immunosuppressive activities.

Over the past two decades, genetic engineering has become an important tool for modifying biological materials to enhance their natural capabilities. For example, in the pharmaceutical area, a number of human proteins (hormones, immunomodulators, enzymes) have been developed by cloning the gene encoding the protein, isolating the protein product and using it directly as a therapeutic agent.

Production of natural metabolites from microbial sources is generally enhanced by strain improvement and process optimization. Classical strain improvement is primarily based on random mutagenesis and subsequent selection for higher producers. Recent development of recombinant DNA technology provides the potential for genetic engineering of microorganisms to enhance the production of metabolites, a more rational alternative to the classical strain improvement techniques.

The following four publications illustrate strain improvement with the use of recombinant DNA technology: 1) Paul L. Skatrud et al., in BIO/TECHNOLOGY, 7, May 1989, pp 477–485, discloses a method of improving production of cephalosporin C in a late step modification by inserting a second copy of a gene encoding a bifunctional protein, expandase/hydroxylase. No disclosure is made to enhance precursor flux. 2) U.S. Pat. No. 5,108,918 relates to a method enhancing production of a secondary metabolite in a bacterial or fungal host by random cloning of a plasmid containing genes for secondary metabolite production. However, this method is non-targeted and non-rational and does not disclose enhancement of precursor flux. 3) A recombinant strain of *Penicillium chrysogenum* was constructed containing extra copies of a gene encoding isopenicillin N synthetase and enhanced enzyme activity showed no improvement in penicillin production, which suggests that this enzyme is not rate-controlling, disclosed by Paul L. Skatrud et al., Poster presentation 1987 Annual Meeting of Society of Industrial Microbiology, Baltimore, Aug. 1987, abstract published in SIM News (1987) 33:77.4). The art has taught that the amount of starch in plant tissue can be enhanced by increasing the expression of a rate controlling enzyme by use of a regulatory variant of the enzyme. There is no disclosure of inserting a second copy of a cloned gene or of enhancing precursor flux.

Studies have shown significant effects of primary (i.e., precursor) metabolites on the production levels of β-lactam antibiotics. For example, addition of the amino acid, lysine, in the fermentation culture of *Penicillium chrysogenum* depressed the level of antibiotics, which can be attributed to the feedback inhibition of an enzyme, i.e., homocitrate synthetase, by lysine as disclosed by J. M. Luengo, et al., *J. Bacteriol.*, 144:869–76 (1980), and P. S. Masurekar, et al., Can. J. Microbiol., 18:1045–1048 (1972). In contrast, addition of the amino acids, lysine and DL-meso-diaminopimelic acid (DAP), in *Streptomyces clavuligerus* stimulated production of the antibiotic cephamycin C as disclosed by S. Mendelovitz, et al., *Antimicrob. Agents Chemother.*, 21:74–84 (1982), possibly by providing a larger precursor pool for biosynthesis of α-aminoadipic acid (α-AAA), or as a result of activation of aspartokinase, the first enzyme involved in lysine biosynthesis via the aspartate pathway.

These publications relate to effect of precursor pools on the cephamycin biosynthesis but no disclosure is made of inserting a second copy of a cloned gene.

SUMMARY OF THE INVENTION

It is believed to be novel in the art to increase the performance of the rate controlling step in a biosynthetic pathway in the production of a precursor to a microbial metabolite by increasing the number of the genes (copy number) encoding the enzyme specifying the rate controlling step.

Briefly, the present invention provides a method for increasing the production of an antimicrobial metabolite comprising the steps of (a) identifying a gene in unaltered chromosomal DNA which encodes the rate controlling step in a biosynthetic pathway in the production of a core material which is a precursor to the antimicrobial metabolite, (b) inserting into the unaltered chromosomal DNA a genetic delivery vehicle carrying at least one of such genes affecting the rate controlling step in the biosynthetic pathway in the production of a core material which is a precursor to the antimicrobial metabolite, thereby producing an altered chromosomal DNA, and (c) introducing the altered chromosomal DNA into the biosynthesis of the antimicrobial metabolite so as to control the reaction rate of the biosynthesis.

In another aspect, the present invention provides a method for increasing the production of an antimicrobial metabolite comprising the steps of: a) identifying the gene in unaltered chromosomal DNA which encodes the rate controlling step in a biosynthetic pathway in the production of a core molecule which is a precursor to the antimicrobial metabolite; and b) inserting, into the unaltered chromosomal DNA, a genetic delivery vehicle (such as a vector, phage, or virus) which carries a gene altering rate controlling step in the biosynthetic pathway in the production of the core molecule which is a precursor to the microbial metabolite that the resulting altered chromosomal DNA has increased genetic material for performing the rate controlling function. The genetic delivery vehicle is generated by inserting at least one exact or modified copy of the gene determining the rate controlling step into a compatible delivery vehicle.

By compatible genetic delivery vehicle is meant, for example, a vector, phage, or virus having appropriate groups on it, so it will insert into a chromosome, for example, by homologous recombination, site-specific integration, or random integration. By core molecule is meant the earliest form of a molecule recognizable as belonging to a specific class.

The antimicrobial metabolite can be produced by any human, plant, fungal, bacterial, or animal cell, preferably by a plant, fungus, or bacteria cell, and more preferably by a bacterial cell of the genus Streptomyces. Most preferably, the antimicrobial metabolite is an antibiotic drug.

In yet another aspect, the invention relates to a chromosome comprising a targeted genetic insertion of DNA which encodes a gene which is involved in a rate controlling step in the biosynthesis of a core molecule which is a precursor to a microbial metabolite.

In a further aspect, this invention relates to a method of insertion of a gene adjacent to an endogenous copy of the gene that specifies a rate controlling biosynthetic step of a core molecule which is a precursor in the production of a microbial metabolite. The method involves cloning a copy of a structural gene (which may include an activator or promotor sequence) and inserting it into an appropriate delivery vehicle (such as a vector, phage, or virus), isolating the resulting modified delivery vehicle and inserting it into a host cell chromosome, for example, by at least one of homologous recombination, site-specific integration, or random integration, to influence the rate controlling step in a biosynthetic pathway in the production of a core molecule which is a precursor to an antimicrobial metabolite.

In a still further aspect, this invention provides a procaryotic or eucaryotic host cell transformed or transfected with a DNA sequence according to the method of the invention stated above, allowing the host cell to express the gene positively affecting the rate controlling step in the production of a microbial metabolite.

In yet another aspect, this invention relates to a method for increasing the production of a precursor (core molecule) to the microbial metabolite which is a product of the rate controlling step and which is a starting material for the microbial metabolite. The precursor can be any building block for a biological material, such as an amino acid, carboxylic acid, sugar, and preferably it is an amino acid.

It is surprising that this genetic manipulation provides a multi-fold increase in the level of the rate controlling enzyme. Further, surprisingly, a unit or multi-unit increase (increase by one or more than one) in the copy number of the gene specifying the rate controlling enzyme in the biosynthesis of a precursor core molecule to a microbial metabolite can provide a multi-fold increase (at least 2–5 times) in the level of production of the microbial metabolite.

It is within the scope of the invention to insert multiple unit increases of the gene encoding the rate controlling enzyme.

DETAILED DESCRIPTION OF PREFERRED EMBODIMENTS OF THE INVENTION

Figure 1:
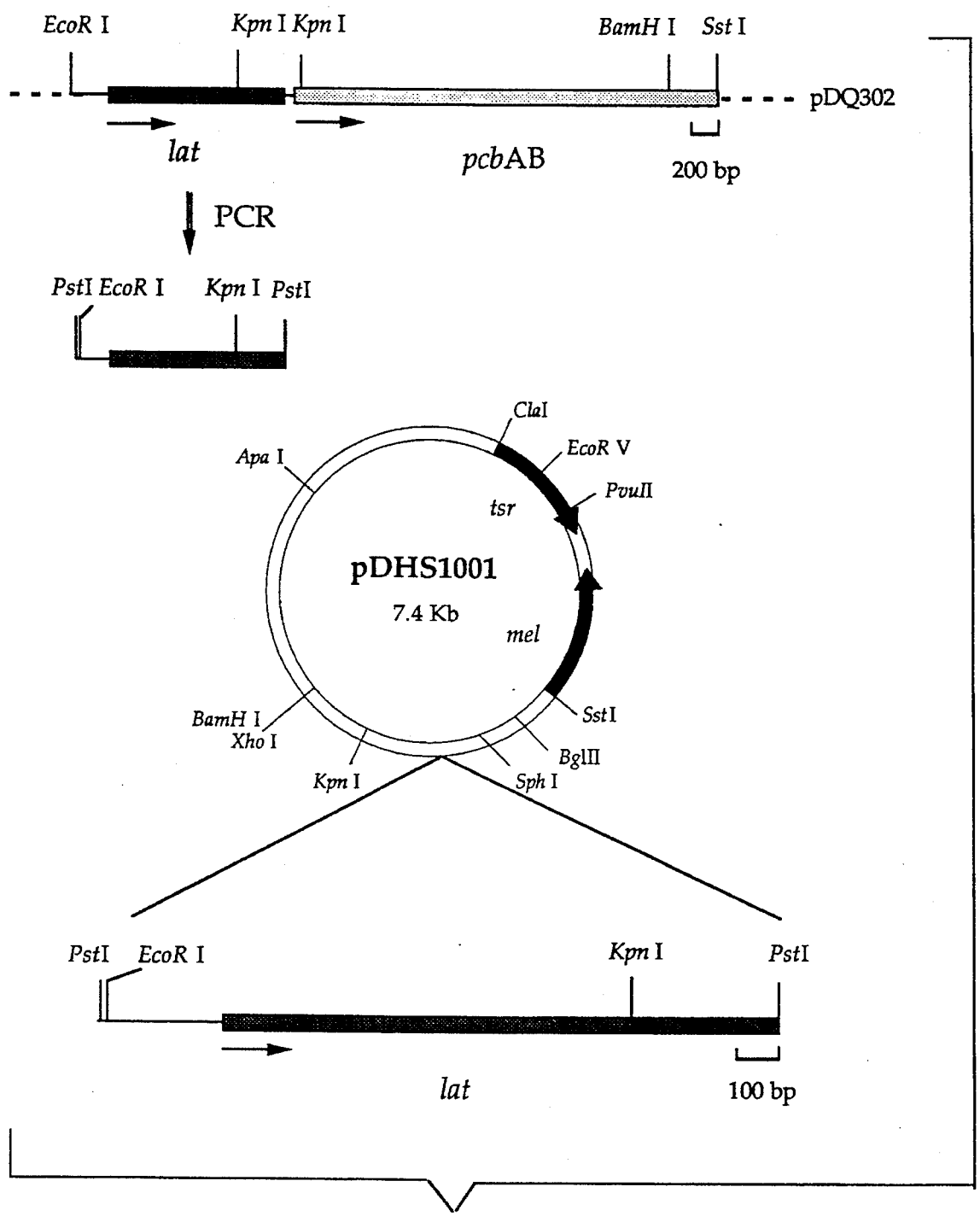
FIG. 1 is a construction of an insertion vector of a preferred embodiment of the invention.

The method for increasing the production of the antimicrobial metabolite which preferably is an antibiotic, most preferably of the genus Streptomyces, involves, in a preferred embodiment, identifying an enzyme which determines the rate controlling step of a precursor core molecule in a biosynthetic pathway leading to production of the antibiotic. The activity of the enzyme responsible for the rate controlling step can then be influenced by genetically altering the DNA encoding the enzyme of the rate controlling step. By genetically altering unaltered DNA is meant modifying chromosomal DNA which includes inserting at least one gene, which can be at least one of a structural gene sequence and a regulatory gene sequence, for the rate controlling enzyme. The modified DNA can be located adjacent or in a nonadjacent location to the endogenous chromosomal gene of the rate controlling enzyme. The altered DNA will then have two or more than two adjacent or nonadjacent identical genes that specify the rate controlling enzyme. By adjacent is meant physically located on the chromosome in a side-by-side location or the genes can be separated by a vector sequence of about 1 to 25 kilobases (kb). By nonadjacent is meant separated by DNA of greater than about 25 kilobases.

Methods for identifying a gene in unaltered chromosomal DNA which encodes the rate controlling step in a biosynthetic pathway are known in the art. A quantitative approach to analyzing biological processes, developed by Higgins, Kascser and Burns, and Heinrich and Rapoport, was based on the so-called control coefficient, in which the effect of a kinetic parameter on the biological response is determined. See 1) Higgins, J., Dynamics and control in cellular parameter on the biological response is determined. See 1) Higgins, J., Dynamics and control in cellular reactions. In Control of Energy Metabolism; Chance, B., Estabrook, R. W., Williamson, J. R., Eds., Academic Press: New York, 1965, pp 13–46; 2) Kacser, H. and Burns, J. A., The control of flux. In Rate Control of Biological Processes, Davies, D. D., Ed., Cambridge University Press: Cambridge, 1973, pp 65–104; and 3) Heinrich, R., and Rapoport, T. A., A linear steady-state treatment of enzymatic chains. General Properties, control and effector strength. Eur. J. Biochem. 1974, 42, 89–95. A recent review article by Liao and Delgado described the theoretical basis and its practical application in designing the experiments. Report by Malmberg et al. applied this concept to identifying the rate-limiting steps in cephalosporin biosynthesis. See Maimberg, L. -H., Sherman, D. H., and Hu, W. -S., Analysis of rate-limiting reactions in cephalosporin biosynthesis, Ann. N.Y. Acad. Sci., 1992, 665, 16–26.

Technology to insert a gene into chromosomal DNA is known in the art. Useful methods include plasmid insertion, insertion of a bacteriophage, or insertion of a viral construct. It is within the scope of this invention to insert a single copy of a gene into chromosomal DNA or to repeat the process and insert multiple copies. Additionally, the genetic delivery vehicle can be constructed to contain one copy or multiple copies of the desired gene which can be inserted as a unit into chromosomal DNA.

In a most preferred embodiment, targeted gene insertion methodology was used to show the effect of altering the quantity of α-aminoadipic acid (α-AAA) concentration on the production levels of β-lactam antibiotics in *Streptomyces clavuligerus*. A high copy plasmid (definition) containing the lysine ε-aminotransferase gene (SEQ ID NO:1) was constructed and used to transform *S. clavuligerus*. The resulting recombinant strain (LHM100) contained an additional complete copy of (SEQ ID NO:1) located adjacent to the corresponding wild-type (definition) gene in the chromosome. Biological activity and production levels of β-lactam antibiotics were at least 2–5 times greater than wild type *S. clavuligerus*. Although levels of lysine ε-aminotransferase (SEQ ID NO:2) were elevated 4-fold in LHM100, the level of ACV synthetase (an enzyme involved in the assembly of the tripeptide precursor for β-lactam antibiotics), whose gene is located just downstream of (SEQ ID NO:1) remained unchanged. These data show that direct alteration of α-AAA precursor concentration resulted in increased antibiotic production. This strategy represents a successful application of metabolic engineering based on theoretical predictions of intracellular precursor concentration in a secondary metabolic pathway.

Reaction equations showing the biosynthetic pathway of cephamycin C from lysine, cysteine, and valine in *S. clavuligerus* is as follows (wherein O-carbamoyl DAC represents O-carbamoyl deacetylcephalosporin C):

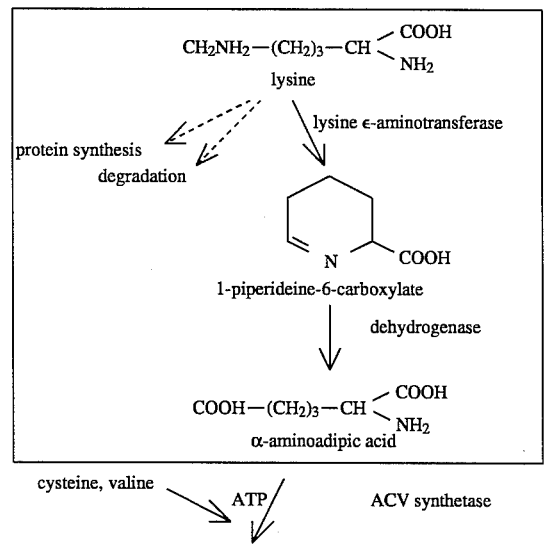

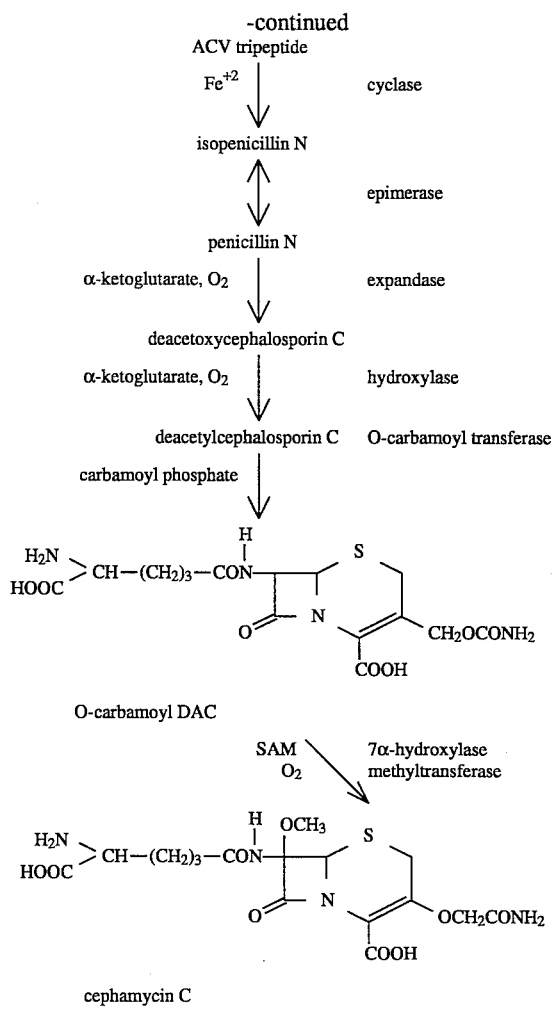

The method of the present invention can be applied to any metabolic pathway where at least one rate controlling step has been or can be determined. It is envisioned within the scope of this invention that this method can be successfully applied to the production of any microbially derived substance. For example, this substance can include any biological monomer or polymer or any organic molecule that is biosynthetically derived, such as a poly-β-hydroxyalkanoate, a polyketide, a shikimate, a saccharide, or a peptide.

An important physiological parameter that influences the level of production of antibiotics by microorganisms is carbon flux from primary to secondary metabolism. In order to increase production levels of specific metabolites by rational design, it is essential to determine inefficient steps in the pathway, which may be targeted and improved through molecular genetic manipulation. This invention describes the second part of a two-part strategy to enhance the production level of any monomer, polymer, or organic molecule that is biosynthetically derived, and most preferably is cephamycin C in *S. clavuligerus*. The first part involved kinetic analysis and simulation of the pathway to predict potential rate-controlling enzymatic steps. The second part, provided by this invention, involves enhancing the identified rate-controlling step through designed pathway construction at the genetic level.

In a most preferred embodiment, this invention discloses an application of a "metabolic engineering" strategy involving the effect of an additional copy of (SEQ ID NO:1) on production of O-carbamoyl deacetylcephalosporin C and cephamycin C in S. clavuligerus. This perturbation resulted in a 5-fold increase in cephamycin C production, which results from a parallel increase in the intracellular level of (SEQ ID NO:2). This evidence makes it apparent that deamination of lysine is one of the key rate-controlling steps in the biosynthesis of cephamycin C. This is consistent with an earlier theoretical prediction in L. Malmberg et al. Ann. N Y Acad. Sci., 665:16–26 (1992), that precursor pools and ACV synthetase are the predicted controlling parameters modulating antibiotic production levels. We found that increasing LAT (SEQ ID NO:2) activity resulted in a metabolic shift of lysine from charging lysine-tRNA for protein synthesis to synthesis of α-AAA. A higher conversion rate from lysine corresponds to a larger α-AAA precursor pool for conversion to ACV tripeptide, thereby increasing antibiotic production. This interpretation was further confirmed by showing that the stimulatory effect of lysine on production of cephamycin C, which was observed during fermentation of the wild-type strain, did not occur in LHM100 (data not shown).

The role of carbon flow in supplying amino acid precursors for antibiotic biosynthesis in S. clavuligerus was first investigated in Y. Aharonowitz et al., J. Bacteriol., 157:337–40 (1984). They showed that aspartokinase deregulated mutants produced five times more cephamycin C than wild-type strain (wt). An additional effect of deregulating the aspartate pathway was an increased intracellular concentration of diaminopimelic acid, which was shown to be stimulatory to antibiotic synthesis. However, the fundamental basis for a higher antibiotic titer by such deregulation, for example, increased metabolic flux for α-AAA, was not investigated. We were interested in determining whether manipulation of both aspartokinase (regulation) and lysine ε-aminotransferase (copy number) results in increased levels of intracellular α-AAA.

Our method for increasing the copy number of lat by chromosomal insertion was chosen as least likely to cause pleiotropic effects on the cephamycin C biosynthetic pathway or on the developmental life cycle of S. clavuligerus. We found that control experiments with pIJ702 (described below) alone resulted in consistently lower levels (up to 20%) of antibiotic production. D. I. Thomas et al., J. Gen. Microbiol., 137:2331–2337 (1991), has shown that plasmid effects are common in antibiotic producing streptomycetes and often lead to lower overall yields of secondary metabolites. Although pIJ702 is not known generally to undergo chromosomal integration or mediate homologous recombination in Streptomyces, an earlier study by A. L. Demain et al., Biochemistry and Genetics of Cephamycin Formation by Streptomyces clavuligerus, in Proceedings of 5th European Congress on Biotechnology, 1990, Copenhagen, Munksgaard, suggested that such an event can occur in the S. clavuligerus chromosome. It remains unclear why a single additional copy of lat (SEQ ID NO:1) leads to a corresponding 4-fold average increase in LAT (SEQ ID NO:2) activity. Based on the location of lat within the integrated copy of pDHS1001 (in LHM100, defined below), it is conceivable that considerable transcriptional readthrough occurs from the pIJ702 rep region that is adjacent to the PstI cloning site chosen for this work. The rep region of pIJ702 has been described in K. Kendall et al., J. Bacteriol., 170:4634–4651 (1988). Alternatively, a potential monocistronic transcript corresponding to the upstream lat (SEQ ID NO:1) mRNA may have enhanced stability and thus an increased rate of translation.

M. B. Tobin, et al., J. Bacteriol., 173: 6223–6229 (1991), has shown that the presumed pcbAB gene encoding ACV synthetase in S. clavuligerus is located adjacent to lat (SEQ ID NO:1) and is separated by a 125 basepairs (bp) noncoding region of DNA. As disclosed by M. B. Tobin et al., J. Bacteriol., 173:6223–6229 (1991), analysis of the DNA sequence in this region showed that an inverted repeat, corresponding to a potential transcriptional terminator, separates the two genes. The significance of this repeat has not been determined, and there is contradictory evidence as reported by Jensen, S. E., 1993, Personal communication, and J. B. Piret et al., Appl. Microbiol Biotechnol., 32:560–567 (1990), as to whether lat(SEQ ID NO:1)/pcbAB comprises a polycistronic message. This was potentially significant to our expression strategy because transcriptional activation of a lat(SEQ ID NO:1)/pcbAB polycistronic message could have led to the concomitant increase in both LAT (SEQ ID NO;2) and ACV synthetase activities. This would have complicated our analysis concerning the role of precursor flux in determining cephamycin C production, since ACV synthetase is predicted to be a key rate-controlling step as well. However, our analysis has shown that the contribution from ACV synthetase is insignificant since there was no increase in the level of this enzyme in LHM100.

L. H. Malmberg et al., Unpublished data, has shown that LHM100 accumulates 80% more α-AAA in the fermentation broth than wild-type S. clavuligerus, indicating that the intracellular concentration of α-AAA may be higher in LHM100. Addition of lysine to the LHM100 fermentation medium did not stimulate the antibiotic production rate, suggesting that the intracellular pool of α-AAA in LHM100 may be in excess. Specifically, the intracellular concentration of α-AAA exceeds its Km value. Therefore, addition of lysine will not increase the production of cephamycin C when ACV synthetase is saturated with α-AAA. Based on this observation and our previous analysis showing ACV synthetase as a predicted rate-controlling enzyme in the cephamycin C secondary metabolic pathway, it is believed that in the wild-type strain both LAT (SEQ ID NO:2) and ACV synthetase are the rate-controlling enzymes. However, in LHM100 ACV synthetase alone becomes the primary rate-controlling enzyme. In order to improve further the biosynthesis of cephamycin C in LHM100, the metabolic flux from precursors to ACV tripeptide can be relieved by increasing ACV synthetase activity. Thus, it becomes important to examine the effect of increasing ACV synthetase activity in both the wild-type and LHM100 strains of S. clavuligerus. Augmentation of ACV synthetase activity may allow additional control and increased production of cephamycin C.

The method and materials of the present invention are useful to provide increased yields of desired biologically synthesized materials. Such material include, for example, antibiotics of the β-lactam class including cephamycin C, cephalosporin C, penicillin V, and penicillin G; antibiotics of the polyketides such as tetracylines, erythromycin, and monensin; antibiotics of the class amino glycocides, including streptomycin; antibiotics of the shikimate class including mitomycin C, and ansamycins; and antibiotics of the peptide class including bacitracin, and cyclosporin A.

Objects and advantages of this invention are further illustrated by the following examples, but the particular materials and amounts thereof recited in these examples, as well as other conditions and details, should not be construed to unduly limit this invention.

Materials and methods used in the examples of the present invention are disclosed below.

Microorganisms and plasmids. All experiments were conducted using *Streptomyces clavuligerus* NRRL 3585 (ATCC 27064). *Escherichia coli* ESS, a strain supersensitive to β-lactam antibiotics, was a gift of A. L. Demain (Massachusetts Institute of Technology, Cambridge, USA). *Streptomyces lividans* 66 (John Innes strain 1326) and plasmid pIJ702 were kindly provided by D. A. Hopwood (John Innes Institute, Norwich, United Kingdom). Plasmid pDQ302 was generously provided by C. Stuttard (Dalhousie University, Halifax, Nova Scotia, Canada).

Medium and culture conditions. Spores of *S. clavuligerus* were produced on tomato-oatmeal agar (10 g tomato paste, 10 g oatmeal, 12.5 g Bacto agar, and 500 mL water, adjusted to pH 6.8) and stored at −20° C. in 50% glycerol. About $1 \times 10^9$ spores were inoculated into a 100 mL seed culture containing the chemically-defined medium of Y. Aharonowitz et al., *Can. J. Microbiol.*, 25:61–67 (1979), supplemented with 0.1% Bacto yeast extract and 0.1% $NH_4Cl$ and grown at 30° C. and 250 rpm for 40 hours. 30 mL of seed culture was inoculated into 1.5 L chemically defined medium but omitting 3-(N-morpholino)propanesulfonic acid (MOPS). Batch fermentations were carried out in a 2-L Multigen F-2000 fermentor (New Brunswick Scientific Co.), and were maintained at pH 6.9 with 5N KOH and 5M HCl, 30° C. 250 rpm and air sparging rate of 1.5 L/min; foaming was prevented by adding approximately 20 mL of 10% polypropylene glycol 2000 (Dow Chemicals Ltd.) at the beginning of fermentation. Shake flask fermentations were conducted in 2 L baffled Erlenmeyer flasks containing 500 mL chemically-defined medium at 30° C. and 50 rpm. The chemically-defined medium consisted of the following (per liter): glycerol, 10 g; L-asparagine, 2 g; $K_2HPO_4$, 3.5 g; $MgSO_4.7H_2O$, 1.23 g; MOPS, 20.9 g, pH 6.9; and trace salts solution, 1 mL (0.1 g $FeSO_4.7H_2O$, 0.1 g $MnCl_2.4H_2O$, 0.1 g $ZnSO_4.7H_2O$, and 0.1 g of $CaCl_2$ per 100 mL water).

DNA isolation and manipulation. Plasmids from *S. lividans* were obtained by the alkaline lysis method as disclosed in D. A. Hopwood et al., Genetic manipulation of Streptomyces: a laboratory manual, Norwich: The John Innes Foundation (1985). Plasmids from *S. clavuligerus* were isolated by preparing and lysing protoplasts using the alkaline lysis procedure. Total chromosomal DNA from Streptomyces was obtained using the Kirby lytic mixture of D. A. Hopwood et al., Genetic manipulation of Streptomyces: a laboratory manual, Norwich: The John Innes Foundation (1985). DNA manipulations in *E. coli* were performed as described by J. Sambrook et al., Molecular cloning: a laboratory manual, second edition ed. Cold Spring Harbor, N.Y.: Cold Spring Harbor Laboratory Press (1989), and those in Streptomyces were performed as described by D. A. Hopwood et al., Genetic manipulation of Streptomyces: a laboratory manual, Norwich: The John Innes Foundation (1985).

DNA labeling and Southern hybridization. Labeling of DNA was performed by nick translation with [α-$^{32}$P]dCTP (Amersham Corp., Arlington Heights, Ill.), DNase I and DNA polymerase I (Bethesda Research Laboratory, Gaithersburg, Md.). DNA fragments were blotted onto Magna-Graph 0.45 -μm-pore size nylon membrane (Micron. Separations, Inc.). Nylon membranes were incubated in prehybridization buffer (1% nonfat dry milk, 1 mM EDTA, 0.5 mM sodium phosphate, pH 7.2, and 7% SDS) at 65° C. for 20 min. After the addition of the denatured, and labeled probe, hybridization was carried out at 65° C. The filters were washed three times for 10 min in 0.5% nonfat dry milk, 1 mM EDTA, 40 mM sodium phosphate, and 5% SDS at 65° C. three times for 20 min in 1 mM EDTA, 20 mM sodium phosphate, and 1% SDS at 65° C.

Transformation of S. clavuligerus. Culture conditions for preparation of protoplasts was modified according to C. R. Bailey et al., *J. Gen. Microbiol.*, 132: 2945–2947 (1986). About $1 \times 10^8$ spores were inoculated into 50 mL TSB (tryptic soy broth) in a 250 mL baffled flask with a coiled spring, and grown at 26° C. for 48 hours. 2 mL of this culture was then inoculated into a new flask containing 20 mL TSB and 30 mL YEME (D. A. Hopwood et al., Genetic manipulation of Streptomyces: a laboratory manual, Norwich: The John Innes Foundation, 1985) supplemented with 3 mM $MgCl_2$ and 0.5% (w/v) glycine. After 24 hour, mycelia were harvested, and protoplasts were prepared according to B. K. Leskiw et al., *Gene.*, 62: 187–96 (1988). Transformation of protoplasts and regeneration was performed using the procedure of D. A. Hopwood et al., Genetic manipulation of Streptomyces: a laboratory manual, Norwich: The John Innes Foundation (1985), modified by B. K. Leskiw et al., *Gene.*, 62:187–96 (1988), and C. R. Bailey et al., *J. Gen. Microbiol.*, 132:2945–2947 (1986). 25 mL of culture was collected by centrifugation at 3000 ×g for 15 min and washed twice with 10.3% sucrose. The pellet was resuspended in 2 mL of 1 mg/mL lysozyme in P buffer containing 0.3M sucrose, 0.57 mM $K_2SO_4$, 25 mM MOPS, pH 7.2, 1 mL of trace elements (0.04 g $ZnCl_2$, 0.2 g $FeCl_3.6H_2O$, 0.01 g $CuCl_2.2H_2O$, 0.01 g $MnCl_2.4H_2O$, 0.01 g $Na_2B_4O_7.10H_2O$, and 0.01 g $(NH_4)_6Mo_7O_{24}.4H_2O$ per liter), and 1% (w/v) bovine serum albumin (BSA)) and then incubated at 30° C. for 15 min. After triturating three times with a pipette before and after dilution with 2.5 mL P buffer, the protoplast suspension was filtered through a sterile cotton plug. The filtered protoplasts were centrifuged at 1000×g for 10 min, washed three times with P buffer and counted in a hemacytometer. Approximately $1 \times 10^9$ protoplasts were centrifuged and suspended in the drop of P buffer left after decanting the supernatant. The protoplasts were then incubated in a 42° C. water bath for 10 min to inactivate the restriction system in *S. clavuligerus* (C. R. Bailey et al., *J. Gen, Microbiol.*, 157:2945–2947 (1986)). The heated protoplasts were transformed with 1 μg of DNA, immediately mixed with 0.5 mL of 25% (w/v) of polyethylene glycol (PEG 1000), NBS Biologicals, Hatfield, UK, in P minus BSA buffer, and then triturated once using a P1000 pipetman. After 1 min at room temperature, the protoplasts were diluted with 2.5 mL of P buffer, centrifuged at 2000×g for 10 min, and finally resuspended in 1 mL P buffer. The transformed protoplasts were plated on regeneration plates R2YEG (171 g sucrose, 20 g Bacto agar, 5.0 g Bacto yeast extract, 11.0 g sodium glutamate, 1 g casamino acids, 0.1 $K_2SO_4$, 0.05 g $MgSO_4$, 10 mL glycerol, and 2 mL trace salt solution per liter) and incubated at 26° C. After 42 hours, the plates were overlaid with 2.5 mL of R2YEG with 0.6% agar and 50 g/mL of thiostrepton. Thiostrepton-resistant colonies became visible after 4 days; transformants were transferred to thiostrepton-containing tomato-oatmeal sporulation plates after 14 days.

Determination of cell growth. Cell growth was monitored by the optical density of broken mycelium suspension at 595 nm, modified from the procedure by A. F. Brana et al., *J. Gen. Microbiol.*, 132:1305–1317 (1986). 0.5 mL of this cell culture was added to a tube containing 0.5 mL of 2.5M HCl and 3 mL water. The mixture was homogenized by ultrasonification for 30 s. The optical density (OD) of the resulting suspension was then measured. Dilution was taken to maintain an $OD_{595}$ less than 0.6 where a linear correlation between dry cell weight and $OD_{595}$ was observed. One unit of $OD_{595}$ was equivalent to 0.59 mg/mL dry cell weight.

Bioassay of β-lactam antibiotics. Antibiotics were determined by the agar plate diffusion assay, with the *Escherichia coli* ESS as indicator microorganism seeded in nutrient broth with 0.8% agar. Cephalosporin C was used as the standard. One unit of β-lactam produces an inhibition zone equivalent to 1 g of cephalosporin C.

Identification and quantitation of antibiotics by high-performance liquid chromatography. The high pressure liquid chromatography (HPLC) system was a Rainin liquid chromatograph with an HPXL solvent delivery system, Rheodyne Model 7125 sample injector, and Dynamax Absorbance UV-D detector (detected wavelength at 254 nm). 20 μL samples of fermentation were injected on a Alltech Econosil $C_{18}$ 10 μm column (25 cm×4.6 mm) and eluted at a flow rate of 1 mL/min. The two mobile phases used were A (14 mM sodium phosphate buffer containing 3.5 g/L tetrabutylammonium hydrogen sulphate, adjusted to pH 6.5 with NaOH) and B (methanol) (K. Holzhauer-Rieger et al., *J. Chromotograph*, 499:609–615 (1990)). Elution was carried out with a linear gradient over 30 min from 0% B in A to 5% B in A. The peaks corresponding to β-lactam antibiotics were identified and quantified by comparing chromatograms of authentic samples of deacetylcephalosporin C, deacetoxycephalosporin C, O-carbamoyl deacetylcephalosporin C and cephamycin C. The antibiotic standards were gifts of J. R. Miller (Eli Lilly and Co., Indianapolis, Ind.) except cephamycin C which was provided by J. V. Heck (Merck and Co., Rahway, N.J.).

Figure 6A:
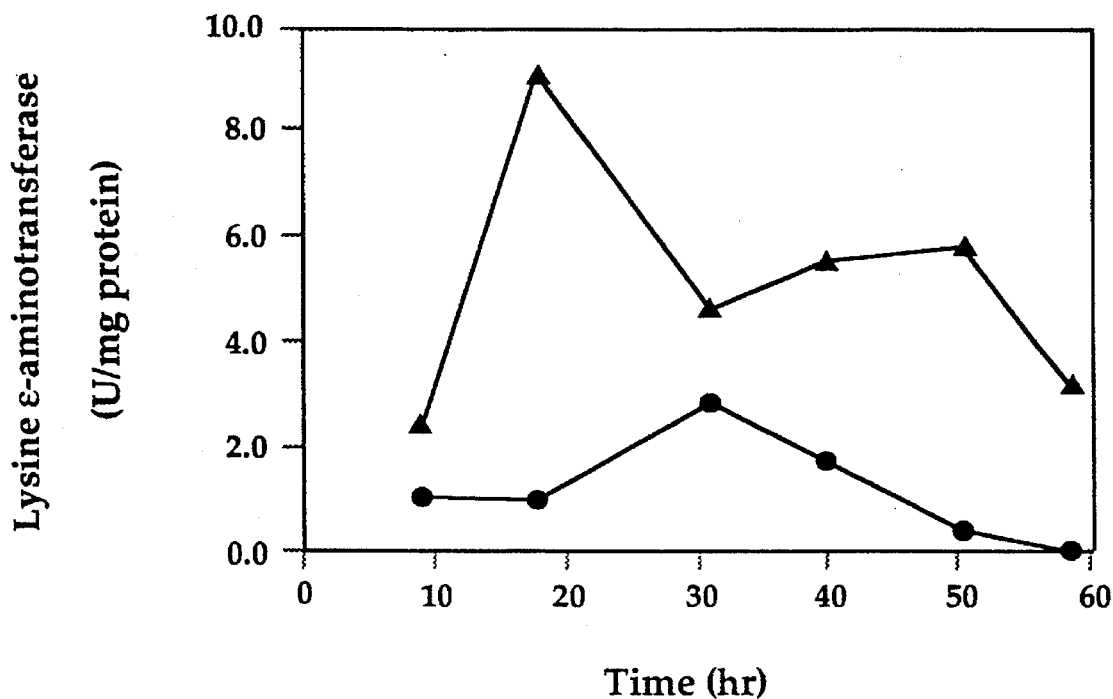
FIG. 6 (A and B) shows the specific activity of two enzymes, lysine ε-aminotransferase LAT (SEQ ID NO.:2) and ACV synthetase, respectively, in the preferred embodiment.
Figure 6B:
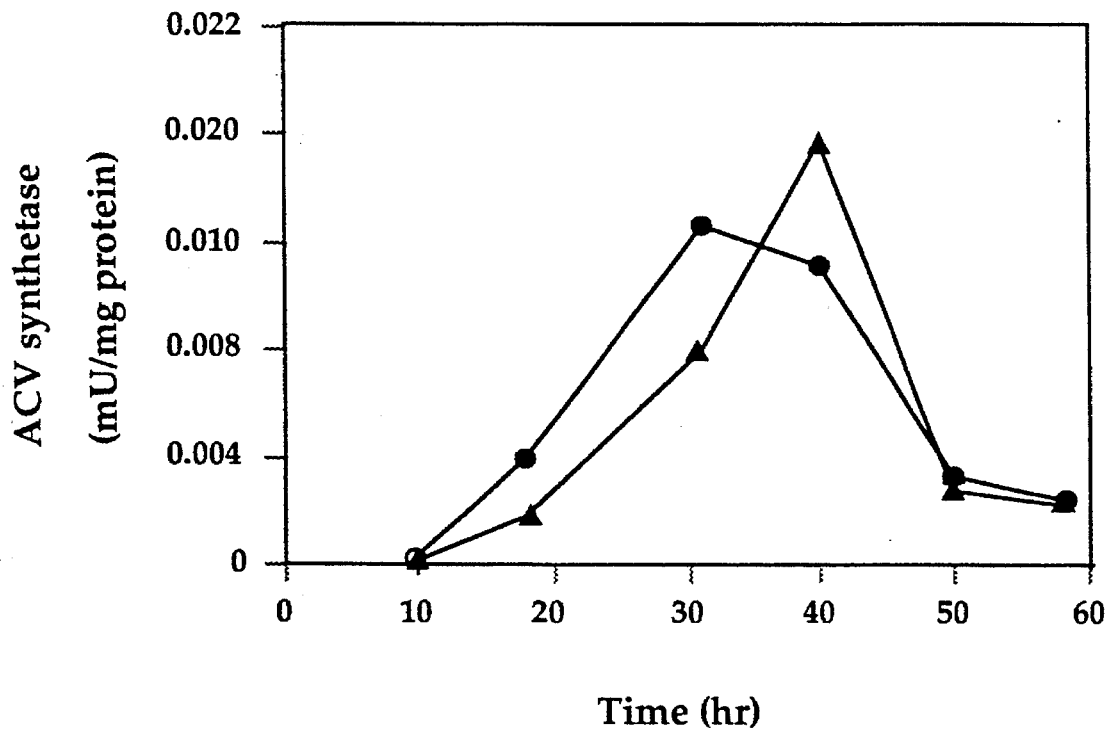
Figure 7A:
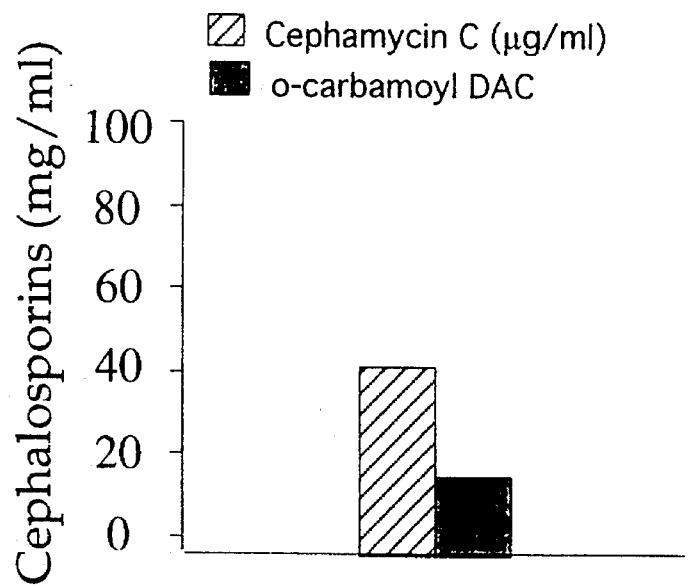
FIG. 7 (A,B and C, D) shows high pressure liquid chromotograms of antibiotic production levels (wild-type comparative strain and the preferred embodiment strain, respectively).
Figure 7B:
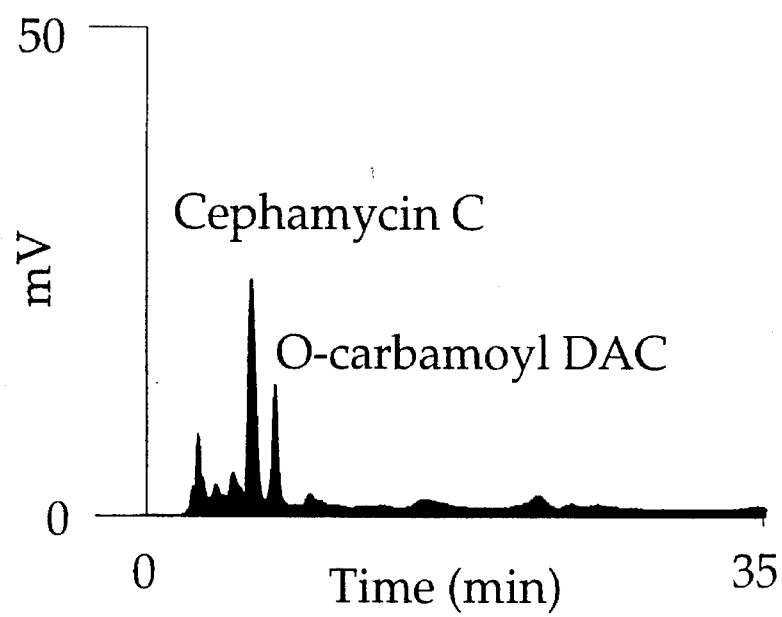
Figure 7C:
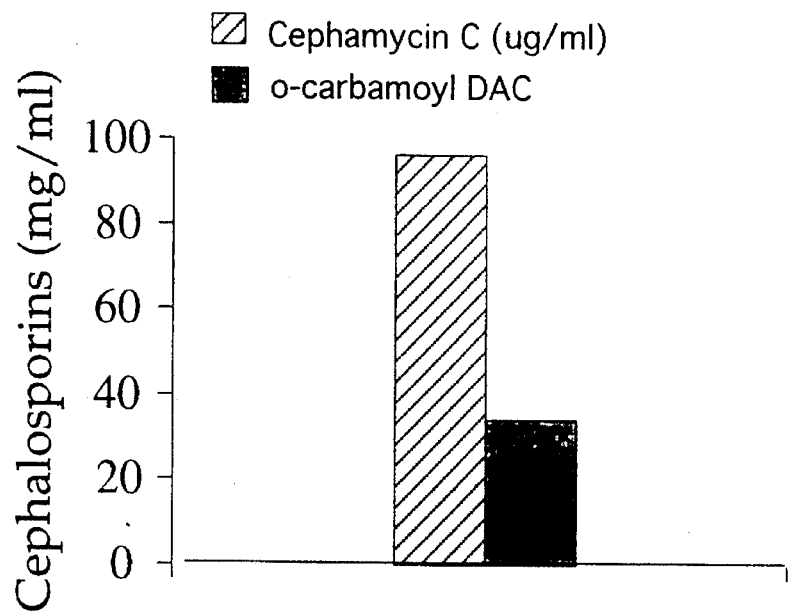
Figure 7D:
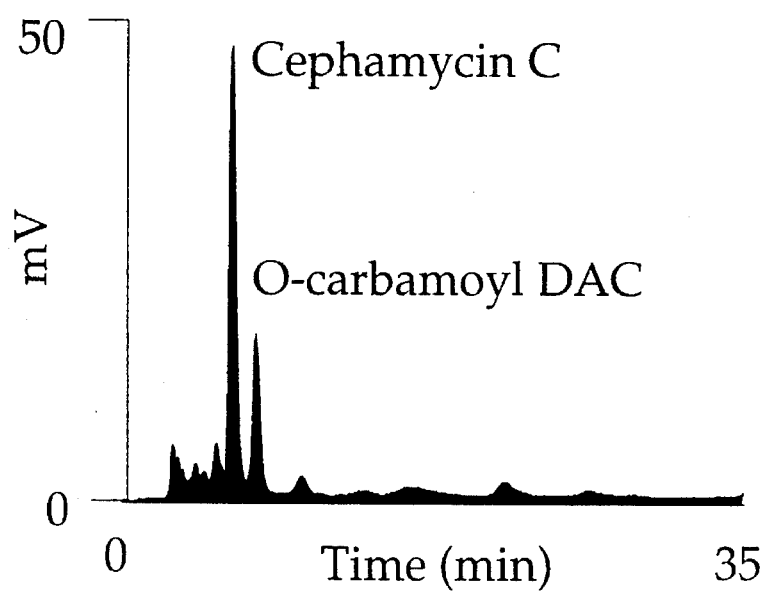

Preparation of cell-free extracts. 25 to 50 mL of sample culture was harvested at the times noted in FIG. 6. Mycelia were washed twice with 0.05M MOPS/KOH (pH 7.5) containing 0.1M KCl and suspended in equal volume of cold 0.1M MOPS/KOH buffer (pH 7.5) containing 20 mM EDTA and 50% glycerol (v/v), and disrupted by sonication in an ice-water bath with a Branson Sonifier (30% strength for 1 min.). Cell debris was removed by centrifugation for 25 min at 14,000 ×g and 4° C. The supernatant fluid was stored at −70° C. and later used in assays of lysine ε-aminotransferase (SEQ ID NO:2) and ACV synthetase activities.

Lysine ε-aminotransferase assay. Cell-free extracts were desalted by passage through a Sephadex G-25™ column (P-10, Pharmacia) using an solution buffer containing 0.2M $K_2HPO_4$—$KH_2PO_4$ buffer (pH 7.5). The desalted cell-free extract was assayed immediately for lysine ε-aminotransferase (SEQ ID NO:2) based on the method of Kern et al. (12).

ACV synthetase assay. The cell-free extract was desalted by passage through a Sephadex G-25 column (P-10, Pharmacia) using an elution buffer containing 0.1M MOPS/KOH (pH 7.5). The desalted cell-free extract was used immediately for ACV synthetase assay developed as disclosed in J. Zhang et al., *FEMS Microbiol. Lett.*, 48 145–50 (1989). ACV concentration was estimated by comparing the peak areas with those of ACV standards, provided by S. E. Jensen (University of Alberta, Edmonton, Alberta, Canada). For both lysine ε-aminotransferase (SEQ ID NO:2) and ACV synthetase assays, one unit of enzyme is defined as the amount producing one μmole of product per minute. Protein in cell extracts was determined by the method disclosed in Lowry et al. (15), using BSA as standard.

Chemicals. o-Aminobenzaldehyde, α-ketoglutarate, lysine, α-aminoadipic acid, and pyridoxal-5-phosphate were purchased from Sigma Chemical Co. (St. Louis, Mo.). Monobromobimane (Thiolyte™ reagent), valine, and cysteine were from Calbiochem (San Diego, Calif.). Ion-pairing reagent, tetrabutylammonium hydrogen sulphate, was purchased from Kodak (Rochester, N.Y.). Restriction endonucleases and other DNA-modifying enzymes were purchased from Bethesda Research Laboratory (Bethesda, Md.). All other fine chemicals were of reagent grade and were purchased from Sigma Chemical Co. (St. Louis, Mo.).

RESULTS

Description of the Drawing

FIG. 1. shows the construction of pDHS1001. The upper portion shows a partial restriction map of the 4.7-kb EcoRI-SstI DNA fragment of *S. clavuligerus* cloned in pDQ302 that contains lat and part of the pcbAB genes. A 1.6-kb PCR fragment containing the lat gene was ligated into the PstI site of pIJ702 to create pDHS1001. The stippled box indicates an open reading frame. The arrows show the direction of transcription. Lat and pcbAB encoded the lysine ε-aminotransferase (SEQ ID NO:2) and ACV synthetase, respectively.

Figure 2:
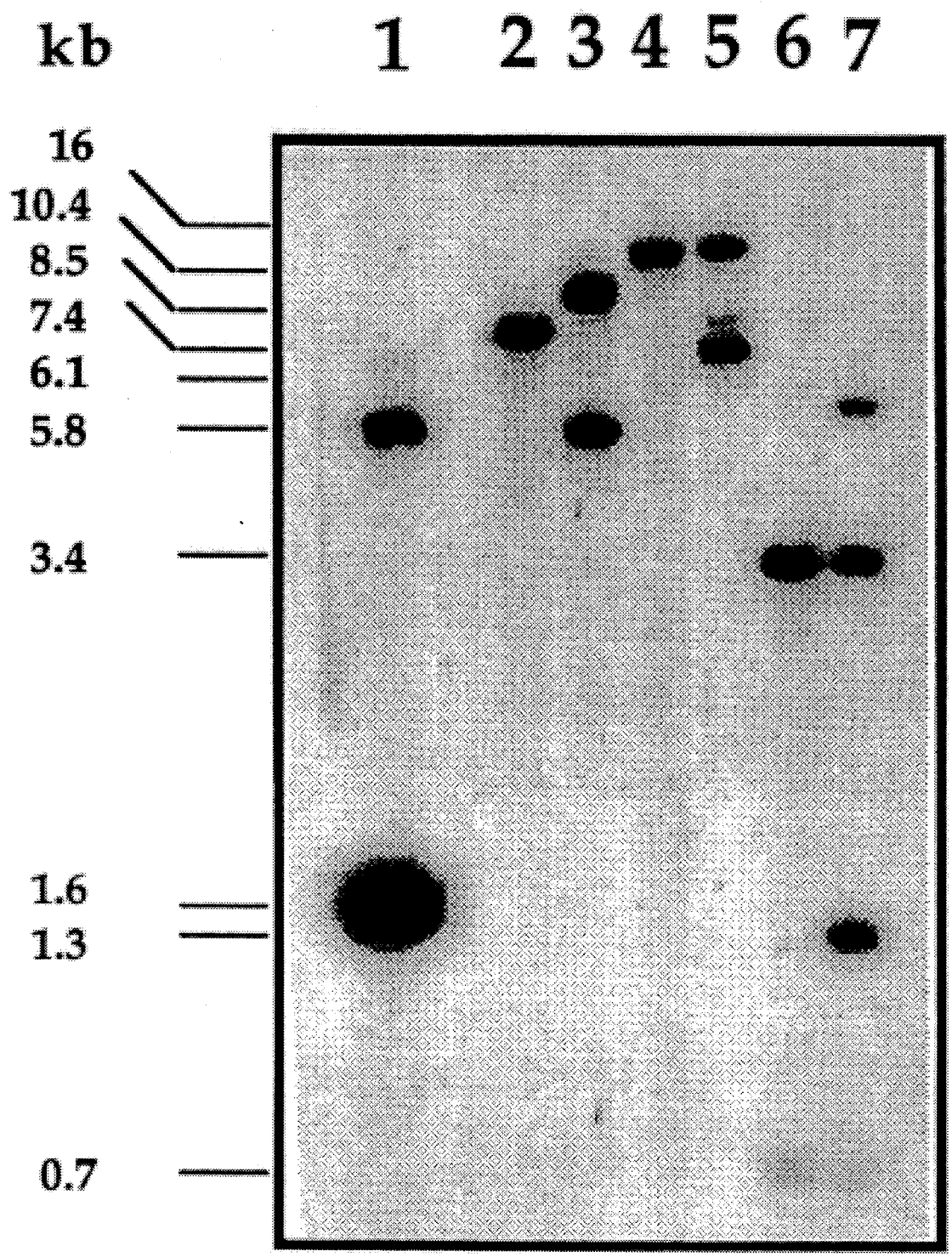
FIG. 2 shows a Southern Blot analysis of altered and unaltered DNA in the preferred embodiment.

FIG. 2 shows Southern blot analysis of the recombinant strain LHM100 (lanes 3, 5, and 7) and its parent strain NRRL3585 (lanes 2, 4, and 6). Total DNA from these strains, digested with BamHI (lane 2 and 3), EcoRI (lanes 4 and 5) or KpnI (lanes 6 and 7), was loaded on a 0.7% agarose gel. pDHS1001 was digested with PstI, resulting in two separate fragments (lane 1). The 5.8-kb fragment contains pIJ702 and the 1.6-kb fragment contains the lat gene. The filter was probed with a 1.6-kb PstI fragment isolated from pDHS1001.

Figure 3:
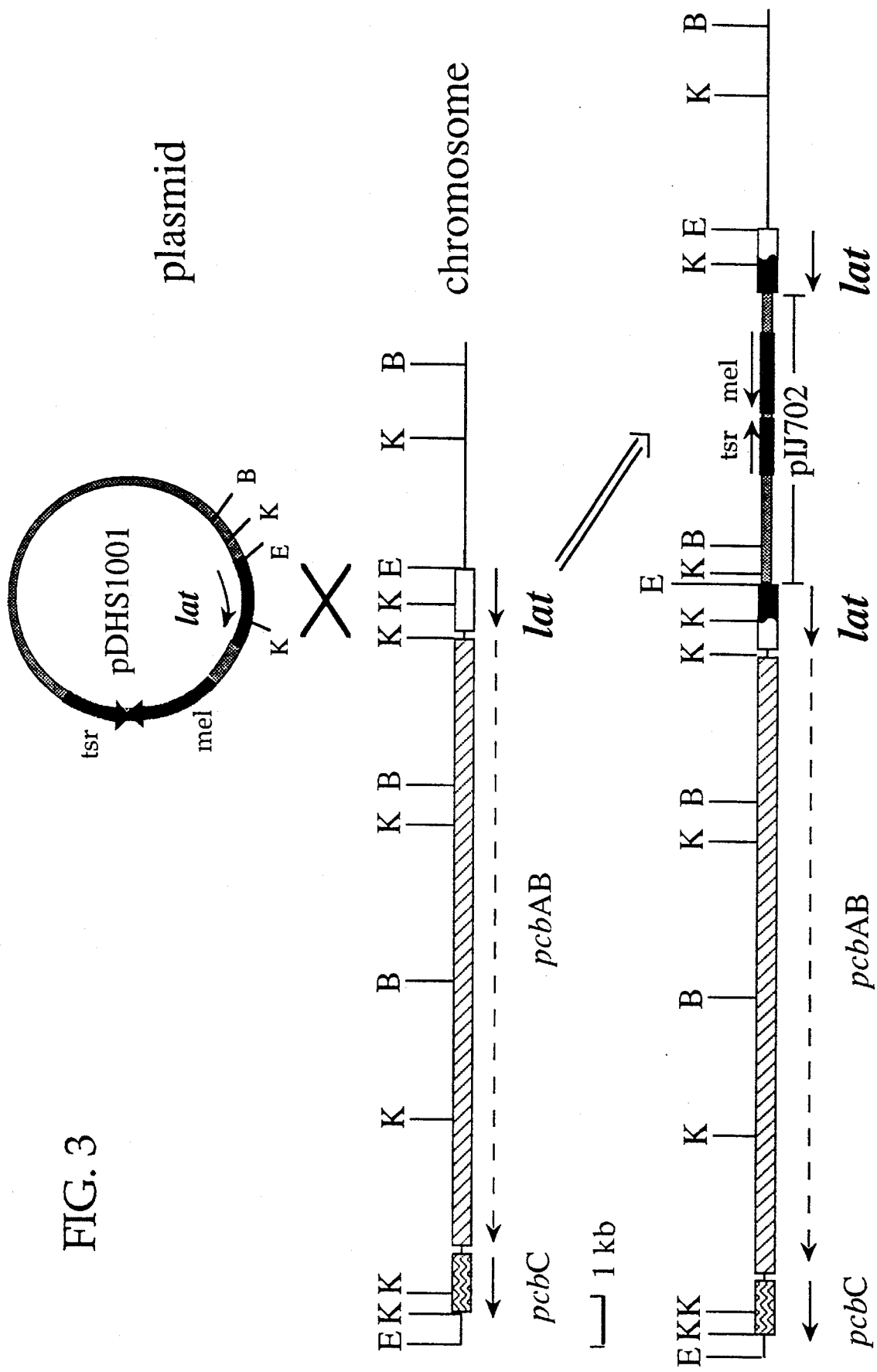
FIG. 3 shows the structure of altered DNA in the preferred embodiment.

FIG. 3 shows integration of pDHS1001 into *S. clavuligerus* chromosome. pDHS1001 was inserted into the lat gene by a single crossover. The resulting LHM100 chromosome contains two copies of lat separated by plasmid pIJ702. The open box indicates the resident lat DNA from the chromosome, and the black box indicates lat DNA from pDHS1001. The solid arrows show the direction of transcription. The dashed line represents the putative transcription of pcbAB. pcbC codes for isopenicillin N synthase.

Figure 4A:
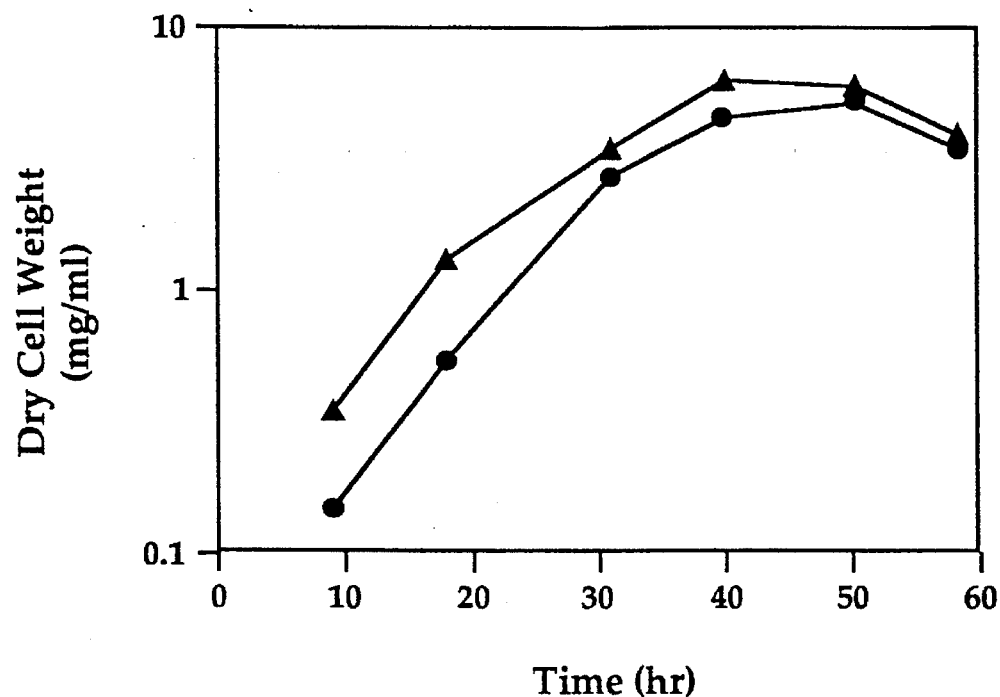
FIG. 4 (A and B) shows the growth and antibiotic production levels, respectively, in the preferred embodiment (0.5 L culture)
Figure 4B:
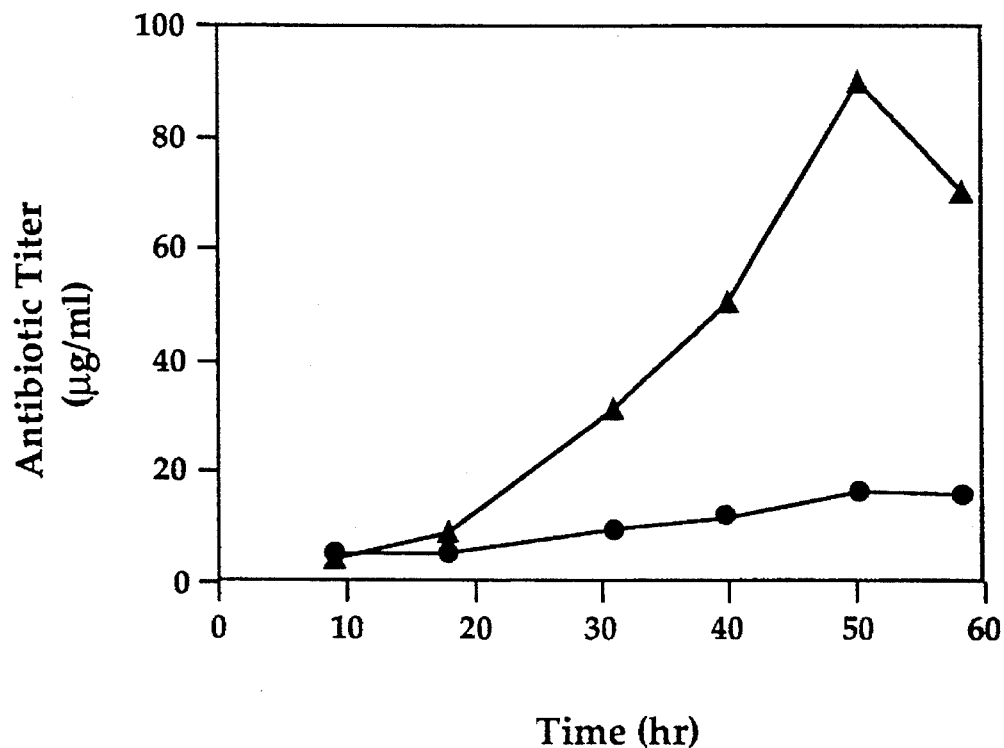

FIG. 4 shows growth (A) and antibiotic production (B) of LHM100 (▲) and the wild-type (●) strains. 500 mL cultures were grown in 2-L baffled shake flasks with seed medium at 30° C. and 250 rpm. Antibiotic concentration was determined by HPLC and expressed as the sum of O-carbamoyl deacetylcephalosporin C and cephamycin C.

FIG. 5 shows growth (A) and antibiotic production (B) of LHM100 (▲) and the wild-type (●) strains. 1.5 liter cultures were grown in a 2-L fermentor with defined medium and 1 μg/mL thiostrepton. Open symbols represent the cephalosporin activity determined by bioassay and filled symbols represent the antibiotic concentration measured by HPLC analysis.

FIG. 6 shows the specific activity of lysine ε-aminotransferase (SEQ ID NO:2)(A) and ACV synthetase (B) from LHM100 (▲) and the wild-type (●) strains during the fermentation. Cell extracts were taken from the same culture shown in FIG. 4.

FIG. 7 shows HPLC chromatograms of antibiotics in the culture broth. Samples were taken from the fermentation culture of the wild-type strain (B) at 120 hour and LHM100 (C) and (D) at 138 hours as shown in FIG. 6. More particularly, FIG. 7A is a bar graph showing relative levels of Cephamycin C and O-carbamoyl DAC produced by wild-type strain *S-clavuligerus*. FIG. 7B is a high pressure liquid chromatographic tracing showing Cephamycin C and O-carbamoyl DAC produced by wild-type strain *S-clavuligerus*. FIG. 7C is a bar graph showing relative levels of Cephamycin C and O-carbamoyl DAC produced by LHM 100 sum of *S-clavuligerus*. FIG. 7D is a high pressure liquid chromatographic tracing showing Cephamycin C and O-carbamoyl DAC produced by LHM100 strain of *S-clavuligerus*.

EXAMPLE 1

Construction of lat (SEQ ID NO:1) integration vector. In order to investigate the effect of increasing precursor flux of α-AAA on cephamycin C production in *S. clavuligerus*, we generated a construct containing the lat (SEQ ID NO:1) gene (1.4 kb) and an additional 228 bp upstream of the translational start codon in the high copy plasmid pIJ702 (see FIG. 1). The upstream region was used to insure inclusion of the lat (SEQ ID NO:1) promoter, which had been inferred through determination of the lat (SEQ ID NO:1) mRNA transcriptional start point (10). Two oligonucleotide primers, CAACCTGCAGTCAGACGCTCTCGGCGACCG (SEQ ID NO:3) and GAGTCTGCAGGAATTCCCCTGAACACGAAG (SEQ ID NO:4), were used to generate the 1.6 kb DNA product comprising lat (SEQ ID NO:1) and the upstream region. The polymerase chain reaction (PCR)-generated DNA was designed to include PstI sites at both ends of the fragment to facilitate subsequent cloning (FIG. 2). pDQ302, an *E. coli*-Streptomyces shuttle vector which includes a 4.7-kb SstI-EcORI fragment from *S. clavuligerus*, contains the lat (SEQ ID NO:1) gene (and has been shown by K. Madduri, et al., *J. Bacteriol.*, 173:985–8 (1991), to express LAT (SEQ ID NO:2) activity in *S. lividans* and *E. coli*) and was used as a template for the PCR (FIG. 1). The amplified fragment was subsequently ligated into the PstI site of pIJ702. Transformation was performed first in *S. lividans*, and pDHS1001 was identified by colony hybridization using the lat (SEQ ID NO:1) PCR product as a hybridization probe (FIG. 1). *S. clavuligerus* protoplasts were then transformed with pDHS1001 isolated from *S. lividans*, using thiostrepton to select transformants containing the desired plasmid.

EXAMPLE 2

Characterization of pDHS1001 transformants in *S. clavuligerus*. Thiostrepton resistant (tsr) transformants of *S. clavuligerus* transformed with pDHS1001 were collected and maintained on 5 μg/mL thiostrepton tomato-oatmeal agar sporulation plates. Two morphologically distinct populations developed following subsequent rounds of sporulation. Population A (LHM101) grew poorly, did not form white mycelium, and produced high levels of melanin, presumably by expression of the mel gene in pDHS1001. Population B (LHM100) grew normally, formed white mycelium, and lacked visible melanin production. LHM100 remained stable after multiple rounds of liquid culture in the absence of thiostrepton, and was stable on agar medium with or without selection by thiostrepton. pDHS1001 was recovered from LHM101, but it was absent from plasmid preparations of LHM100. To address whether pDHS1001 had integrated into the *S. clavuligerus* chromosome, Southern hybridization of genomic DNA from wt *S. clavuligerus* and the tsr strain LHM100, lacking autonomous plasmid, was performed. Initially, the genomic DNA from wt *S. cla-vuligerus* and LHM100 was probed with pIJ702 and showed clearly that pIJ702 was present in the chromosome of strain LHM100 and absent from the wt strain of *S. clavuligerus* (not shown). The observed integration had presumably occurred by homologous recombination between lat in pDHS1001 and the *S. clavuligerus* chromosome. To determine the site of integration and the copy number of pDHS1001, genomic DNA of wt and strain LHM100 was digested with selected restriction enzymes and probed with the 1.6 kb PstI fragment containing lat (FIG. 2). Based on the hybridization patterns and intensities of each band from the wt and strain LHM100, one copy of pDHS1001 was inserted into a site within the cephamycin C gene cluster by single crossover into the resident lat gene (FIG. 3). Although the precise crossover point between resident and plasmid-borne lat (SEQ ID NO:1) genes cannot be determined, it is clear that both copies of the gene are transcribed from right to left as shown in FIG. 3 and are separated by the vector, pIJ702. The relative positions of the mel and tsr genes are shown, although the direct influence that these or other genes contained within pIJ702 may have on transcription of each lat (SEQ ID NO:1) gene is not clear.

EXAMPLE 3

LHM100 produces 2–5 fold higher levels of cephamycin C than wt *S. clavuligerus*. To examine the effect of an additional copy of lat (SEQ ID NO:1) on production of cephamycin C and its immediate precursor O-carbamoyl deacetylcephalosporin C, production levels of each antibiotic in liquid cultures of the wt and recombinant LHM100 strains were determined. Fermentations in shake flasks and 2 liter fermentors indicated that LHM100 produced significantly higher levels of cephamycin C than wt *S. clavuligerus* (FIGS. 4 and 6). Shake flask fermentations consistently gave 5 times greater antibiotic production than wt *S. clavuligerus*, while maintaining essentially identical growth kinetics (see FIGS. 4 and 6). In the 2 liter fermentor, both bioassay and HPLC analysis of the culture broth revealed that LHM100 produced a 2-fold higher level of cephamycin C compared to wt (FIG. 6). The disparity of these two fermentation runs may be due to differences in culture medium used, and in particular, the use of thiostrepton selection in the 2 liter growth medium. Significantly, HPLC analysis of β-lactams showed that the production ratio of the two major β-lactam antibiotics, O-carbamoyl deacetylcephalosporin C and cephamycin C, remained invariant between the wt and recombinant (LHM100) strains (FIG. 7).

In contrast to LHM100, LHM101 which contains pDHS1001 at high copy number as an autonomous plasmid, was found to have no biological activity against the *E. coli* ESS indicator strain. HPLC confirmed that the strain failed to produce antibiotics O-carbamoyldeacetyl cephalosporin C and cephamycin C (data not shown). Significantly, *S. clavuligerus* transformed with pIJ702 alone showed 20% lower levels of antibiotic production. Such plasmid effects have been observed previously in other antibiotic producing streptomycetes as disclosed in D. I. Thomas et al., *J. Gen. Microbiol.*, 137:2331–2337 (1991).

EXAMPLE 4

Figure 5A:
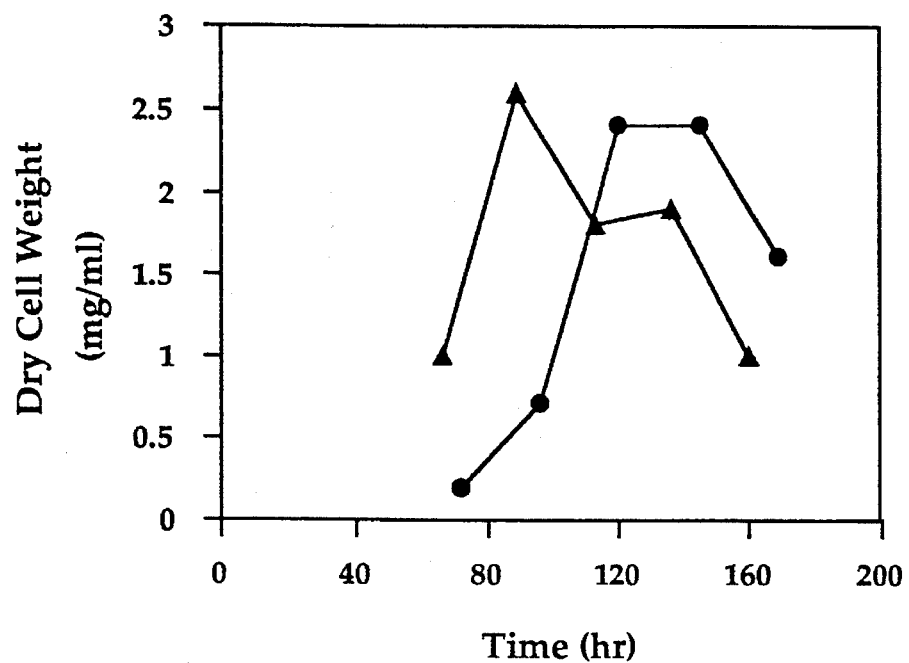
FIG. 5 (A and B) shows the growth and antibiotic production levels, respectively, in the preferred embodiment (1.5 L culture)

LHM100 exhibited four-fold higher lysine ε-aminotransferase (LAT) (SEQ ID NO:2) activity than wt *S. clavuligerus*. To examine if an additional copy of lat (SEQ ID NO:1) resulted in higher activity of lysine ε-aminotransferase (SEQ ID NO:2) in LHM100 compared to wt, enzyme activities produced by these two strains during fermentation were determined. LHM100 showed consistently higher LAT (SEQ ID NO:2) activity than wt *S. clavuligerus* (FIG. 5A). This increase in LAT (SEQ ID NO:2) activity ranged from 2–9 fold during the culture growth and was considerably greater than expected from one additional copy of lat (SEQ ID NO:1) in the cephamycin C gene cluster.

Figure 5B:
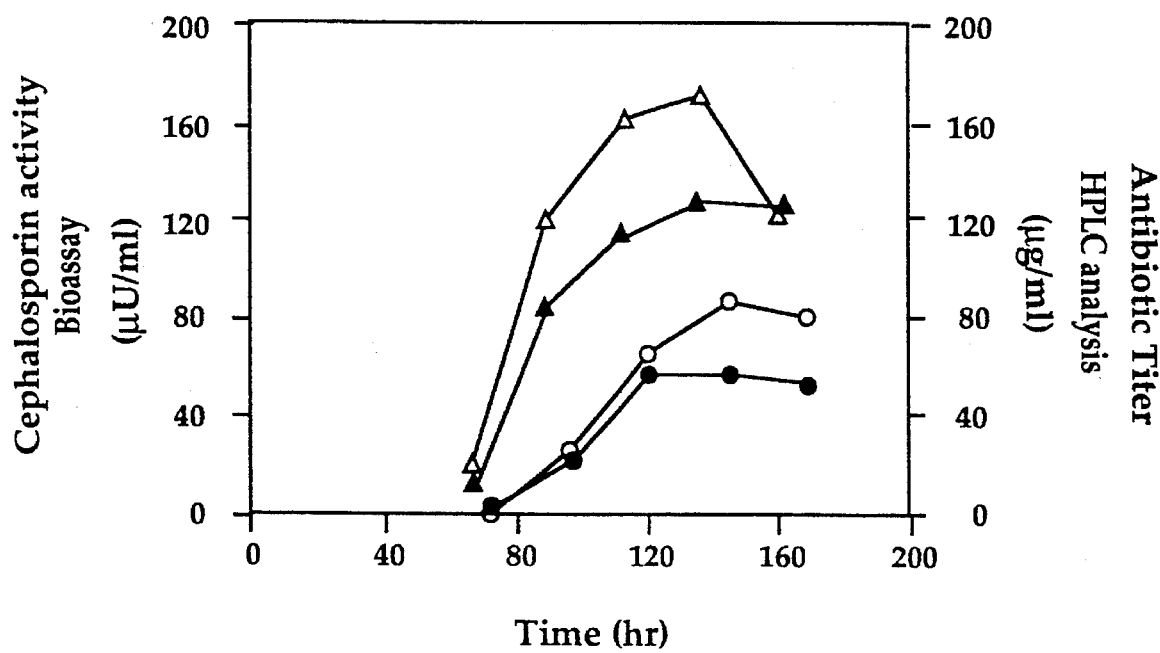

To assess whether transcriptional activation of the presumed lat(SEQ ID NO:1)/pcbAB operon had occurred from a vector promoter in LHM100, with a subsequent increase in ACV synthetase activity, cell-free extracts of the wt and LHM100 strains were also assayed for ACV synthetase activity. HPLC analysis of the cell-free extracts containing ACV synthetase activity from wt and LHM100 showed no increase in enzyme level in LHM100 (FIG. 5B). The data show that transcriptional activation of lat from a promoter within pIJ702 had occurred. However, this activation did not increase the level of ACV synthetase, which was encoded by a gene just downstream of lat (SEQ ID NO:1) (FIG. 3).

Various modifications and alterations of this invention will become apparent to those skilled in the art without departing from the scope and spirit of this invention, and it should be understood that this invention is not to be unduly limited to the illustrative embodiments set forth herein.

We claim:

1. In a method of practicing a β-lactam antibiotic comprising culturing a microorganism that naturally produces the antibiotic, the improvement comprising inserting one or more copies of a gene encoding an enzyme lysine ε-aminotransferase (LAT) into a chromosome of the microorganism.

2. The method according claim 1 wherein at least one of said one or more copies is inserted adjacent to an endogenous chromosomal gene which encodes LAT.

3. The method according to claim 1 wherein at least one of said one or more copies is inserted non-adjacent to an endogenous chromosomal gene which encodes LAT.

4. The method according to claim 1, wherein said β-lactam antibiotic is a natural metabolite.

5. The method according to claim 1 wherein said β-lactam antibiotic is O-carbamoyl deacetylcephalosporin C.

6. The method according to claim 1 wherein said β-lactam antibiotic is cephamycin C.

7. The method according to claim 1 which produces a precursor, β-aminoadipic acid, to a core molecule in the biosynthetic pathway for said β-lactam antibiotic.

8. The method according to claim 7 wherein said core molecule is isopenicillin N.

9. The method according to claim 1 wherein the production of said β-lactam antibiotic is increased at least two-fold relative to the production of β-lactam antibiotic by wild type

*S. clavuligerus.*

10. The method according to claim 1 wherein said copies of a gene are introduced into the microorganism by a delivery vehicle which is selected from the group consisting of vectors, phages, and viruses.

11. The method of claim 1 wherein the one or more copies of the gene encoding LAT are inserted into the chromosome of the microorganism.

12. The method according to claim 1 wherein the production of said β-lactam antibiotic is increased in the range of two-fold to five-fold relative to the production of β-lactam antibiotic by wild-type *S. clavuligerus*.

13. The method according to claim 1 wherein the activity of LAT is increased in the range of two-fold to nine-fold relative to its activity in wild-type *S. clavuligerus*.

14. The method according to claim 1 wherein said β-lactam antibiotic is cephalosporin C.

15. The method according to claim 1 wherein said β-lactam antibiotic is at least one of penicillin V and penicillin G.

16. A host cell which is a β-lactam antibiotic-producing microorganism in which one or more copies of a gene encoding LAT are introduced into the host cell chromosome, said host cell being capable of producing said β-lactam antibiotic in an amount that is increased by at least two-fold compared to the amount of said β-lactam antibiotic produced by wild-type *S. clavuligerus*.

17. The host cell according to claim 16 wherein said LAT catalyzes a step in the biosynthesis of α-aminoadipic acid (α-AAA), a precursor to the core molecule of said β-lactam antibiotic.

18. The host cell according to claim 16 wherein said LAT catalyzes a step in the synthesis of amino acid precursor α-amino adipic acid which is incorporated into ACV tripeptide, a precursor to the core molecule of said β-lactam antibiotic.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1601 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GAATTCCCCT  GAACACGAAG  CTGAGCAACA  GCTCGTCACG  CGCTCCCGAG  CTGGCCATTC       60
AGGGCAGTTC  ACAAAGAGCC  ATCGAGAGGC  GTCCGAGAGA  GCTGGAAGAG  GGGTCCAAGA      120
GCATGGTGGG  TCATTATTGT  GATCCTAAAA  TGTCCAGTTC  ACCGCCATGA  CAGCAGAGGC      180
TGGAAAGTCC  CCCATAATTC  AGCCTGATCC  CCCAGGAGTT  CTCACCCATG  GGCGAAGCAG      240
CACGCCACCC  CGACGGCGAT  TTCTCGGACG  TGGGAAACCT  CCACGCTCAG  GACGTGCACC      300
AGGCACTTGA  GCAGCATATG  CTCGTCGACG  GGTACGACCT  CGTTCTCGAC  CTCGACGCCA      360
GCTCCGGCGT  CTGGCTCGTC  GACGCCGTCA  CCCAGAAGCG  GTATCTCGAC  CTCTTTTCCT      420
TCTTTGCCTC  GGCGCCGCTC  GGAATCAACC  CGCCCAGCAT  TGTCGAGGAC  CCGGCATTCA      480
TGCGGGAGCT  GGCCGTGGCC  GCGGTCAACA  AGCCGTCGAA  CCCCGATCTT  TATTCGGTGC      540
CGTACGCCCG  TTTCGTCAAG  ACCTTCGCCC  GGGTCCTCGG  CGACCCCCGG  CTGCGGCGGC      600
TGTTCTTCGT  GGACGGCGGG  GCGCTGGCCG  TGGAGAACGC  GCTCAAGGCG  GCCCTCGACT      660
GGAAGGCCCA  GAAGCTGGGC  CTCGCCGAGC  CGGACACCGA  CCGGCTCCAG  GTGCTGCATC      720
TGGAGCGCTC  GTTCCACGGC  CGCAGCGGCT  ACACCATGTC  GCTGACGAAC  ACCGAGCCGT      780
CCAAGACCGC  CCGCTTCCCC  AAGTTCGGCT  GGCCACGGAT  CTCGTCCCCC  GCCCTCCAGC      840
ACCCGCCGGC  CGAGCACACC  GGCGCCAACC  AGGAGGCCGA  GCGACGGGCG  CTGGAGGCCG      900
CCCGGGAGGC  GTTCGCAGCG  GCGGACGGCA  TGATCGCCTG  CTTCATCGCG  GAGCCCATCC      960
AGGGCGAGGG  CGGCGACAAC  CACCTCAGCG  CGGAGTTCCT  CCAGGCCATG  CAGCGGCTCT     1020
GCCACGAGAA  CGACGCCCTG  TTCGTCCTGG  ACGAGGTGCA  GAGCGGCTGC  GGCATCACCG     1080
GTACCGCCTG  GGCCTACCAG  CAGCTCGGCC  TCCAGCCCGA  CCTGGTGGCC  TTCGGCAAGA     1140
AGACCCAGGT  CTGCGGGGTG  ATGGGCGGCG  GCCGGATCGA  CGAGGTCCCC  GAGAACGTCT     1200
TCGCCGTCTC  CTCCCGGATC  AGCTCCACCT  GGGGCGGCAA  CCTCGCCGAC  ATGGTCCGCG     1260
CCACCCGGCT  GCTGGAGACG  ATCGAGCGCA  CCCAGGTCTT  CGACACCGTC  GTCCAGCGCG     1320
```

-continued

```
GCAAGTACTT CCGGGACGGC CTGGAGGACC TGGCCGCCCG CCACCCCTCC GTCGTGACCA    1380

ACGCCCGCGG CCGGGGCCTG ATGTGCGCGG TCGACCTGCC GGACACCCGG ACCCGCAATG    1440

AGGTGCTGCG GCTCATGTAC ACGGAGCACC AGGTCATCGC CCTGCCCTGC GGCGGGCGCA    1500

GCCTCCGGTT CCGCCCCGCG CTGACGATCG CGGAGCACGA GATCGACCAG GCCCTTCAGG    1560

CGCTGGCGAG CAGTGTCACG CCGGTCGCCG AGAGCGTCTG A                        1601
```

(2) INFORMATION FOR SEQ ID NO:2:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Gly Glu Ala Ala Arg His Pro Asp Gly Asp Phe Ser Asp Val Gly
 1               5                  10                  15

Asn Leu His Ala Gln Asp Val His Gln Ala Leu Glu Gln His Met Leu
            20                  25                  30

Val Asp Gly Tyr Asp Leu Val Leu Asp Leu Asp Ala Ser Ser Gly Val
        35                  40                  45

Trp Leu Val Asp Ala Val Thr Gln Lys Arg Tyr Leu Asp Leu Phe Ser
    50                  55                  60

Phe Phe Ala Ser Ala Pro Leu Gly Ile Asn Pro Pro Ser Ile Val Glu
65                  70                  75                  80

Asp Pro Ala Phe Met Arg Glu Leu Ala Val Ala Ala Val Asn Lys Pro
                85                  90                  95

Ser Asn Pro Asp Leu Tyr Ser Val Pro Tyr Ala Arg Phe Val Lys Thr
            100                 105                 110

Phe Ala Arg Val Leu Gly Asp Pro Arg Leu Arg Arg Leu Phe Phe Val
        115                 120                 125

Asp Gly Gly Ala Leu Ala Val Glu Asn Ala Leu Lys Ala Ala Leu Asp
    130                 135                 140

Trp Lys Ala Gln Lys Leu Gly Leu Ala Glu Pro Asp Thr Asp Arg Leu
145                 150                 155                 160

Gln Val Leu His Leu Glu Arg Ser Phe His Gly Arg Ser Gly Tyr Thr
                165                 170                 175

Met Ser Leu Thr Asn Thr Glu Pro Ser Lys Thr Ala Arg Phe Pro Lys
            180                 185                 190

Phe Gly Trp Pro Arg Ile Ser Ser Pro Ala Leu Gln His Pro Pro Ala
        195                 200                 205

Glu His Thr Gly Ala Asn Gln Glu Ala Glu Arg Arg Ala Leu Glu Ala
    210                 215                 220

Ala Arg Glu Ala Phe Ala Ala Ala Asp Gly Met Ile Ala Cys Phe Ile
225                 230                 235                 240

Ala Glu Pro Ile Gln Gly Glu Gly Gly Asp Asn His Leu Ser Ala Glu
                245                 250                 255

Phe Leu Gln Ala Met Gln Arg Leu Cys His Glu Asn Asp Ala Leu Phe
            260                 265                 270

Val Leu Asp Glu Val Gln Ser Gly Cys Gly Ile Thr Gly Thr Ala Trp
        275                 280                 285

Ala Tyr Gln Gln Leu Gly Leu Gln Pro Asp Leu Val Ala Phe Gly Lys
```

|       |     |     |     |     |     |     |     |     |     |     |     |     |     |     |
|-------|-----|-----|-----|-----|-----|-----|-----|-----|-----|-----|-----|-----|-----|-----|
|       |     |     |     |     | 290 |     |     |     |     | 295 |     |     |     | 300 |
| Lys 305 | Thr | Gln | Val | Cys | Gly 310 | Val | Met | Gly | Gly | Gly 315 | Arg | Ile | Asp | Glu | Val 320 |
| Pro | Glu | Asn | Val | Phe 325 | Ala | Val | Ser | Ser | Arg 330 | Ile | Ser | Ser | Thr | Trp 335 | Gly |
| Gly | Asn | Leu | Ala 340 | Asp | Met | Val | Arg | Ala 345 | Thr | Arg | Leu | Leu | Glu 350 | Thr | Ile |
| Glu | Arg | Thr 355 | Gln | Val | Phe | Asp | Thr 360 | Val | Val | Gln | Arg | Gly 365 | Lys | Tyr | Phe |
| Arg | Asp 370 | Gly | Leu | Glu | Asp | Leu 375 | Ala | Ala | Arg | His | Pro 380 | Ser | Val | Val | Thr |
| Asn 385 | Ala | Arg | Gly | Arg | Gly 390 | Leu | Met | Cys | Ala | Val 395 | Asp | Leu | Pro | Asp | Thr 400 |
| Arg | Thr | Arg | Asn | Glu 405 | Val | Leu | Arg | Leu | Met 410 | Tyr | Thr | Glu | His | Gln 415 | Val |
| Ile | Ala | Leu | Pro 420 | Cys | Gly | Gly | Arg | Ser 425 | Leu | Arg | Phe | Arg | Pro 430 | Ala | Leu |
| Thr | Ile | Ala 435 | Glu | His | Glu | Ile | Asp 440 | Gln | Ala | Leu | Gln | Ala 445 | Leu | Ala | Ser |
| Ser | Val 450 | Thr | Pro | Val | Ala | Glu 455 | Ser | Val |

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CAACCTGCAG  TCAGACGCTC  TCGGCGACCG                               30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GAGTCTGCAG  GAATTCCCCT  GAACACGAAG                               30